United States Patent [19]

Paulson, Jr.

[11] Patent Number: 4,634,280
[45] Date of Patent: Jan. 6, 1987

[54] METHOD FOR MEASURING SHAPE PARAMETERS OF YARN

[75] Inventor: Charles M. Paulson, Jr., Wilmington, Del.

[73] Assignee: E. I. DuPont De Nemours and Company, Wilmington, Del.

[21] Appl. No.: 673,874

[22] Filed: Nov. 21, 1984

[51] Int. Cl.⁴ .............................................. G01B 11/04
[52] U.S. Cl. ................................... 356/385; 356/429; 250/571
[58] Field of Search ............... 356/384, 385, 429, 430, 356/238; 250/559, 571, 572

[56] References Cited

U.S. PATENT DOCUMENTS 4,091,368  5/1978  Schwartz ............................ 250/571
4,389,575  6/1983  Cole .................................... 356/430

FOREIGN PATENT DOCUMENTS

2451533  5/1976  Fed. Rep. of Germany ...... 356/238
1445915  8/1976  United Kingdom ................ 356/238
2064106  6/1981  United Kingdom ................ 356/238

Primary Examiner—F. L. Evans
Assistant Examiner—Joel L. Harringa

[57] ABSTRACT

A method for determining a parameter that characterizes the cross sectional shape of a running multilobal filament or yarns thereof, by light scattering analysis. The analysis is based on detecting and measuring the intensity of light scattered from the yarn in the plane of the incident beam which is oriented perpendicularly to the longitudinal axis of the yarn. By comparing the intensity of the scattered light with previously measured standard values for the particular yarn geometry being measured, using correlation techniques, the average cross sectional shape parameter can be determined.

7 Claims, 9 Drawing Figures

METHOD FOR MEASURING SHAPE PARAMETERS OF YARN

BACKGROUND OF THE INVENTION

This invention relates generally to the production of filamentary structures and, more particularly, it relates to a method for determining the average cross-sectional characteristics of a yarn or filament from light scattering analysis.

Light reflectance measurements are known to correlate with certain yarn physical parameters, such as bulk, as disclosed by Van Veld in U.S. Pat. No. 3,471,702, but owing to a lack of knowledge about reflection of light from yarn or filaments and the effect the cross-sectional characteristics of such yarns or filaments have on such reflection, a satisfactory method for characterizing average cross-sectional shape of multilobal yarns or filaments has not been devised.

SUMMARY OF THE INVENTION

It has now been discovered that detecting light scattered from a yarn bundle of multilobal filaments having a longitudinal axis oriented perpendicular to the plane containing both the incident and scattered beams of light provides a most appropriate method for obtaining a parameter that characterizes cross-sectional shape of multilobal filaments. One of the parameters of interest, average modification ratio (MR) is measured by moving a bundle of multilobal filaments in a path under tension, then directing an incident beam of light onto the bundle in a plane perpendicular to the filament bundle path. The light scattered from the bundle in the plane of the incident beam is detected at at least one location angularly positioned anywhere from 6 to 176 degrees from the location of the incident beam and its intensity measured. The intensities thus measured are analyzed to determine the average modification ratio of the filaments in the bundle.

In a preferred embodiment the light scattered from the bundle is detected at two closely spaced locations angularly displaced about 128 degrees from the incident beam.

Throughout the specification and claims the terms "filament" and "yarn" will be used in their usual and accepted sense, i.e., "filament" refers to an individual textile fiber of extreme length and "yarn" refers to a bundle of filaments having some degree of cohesion. By the term "modification ratio" (MR) is meant the ratio of the radius (Ro) of a circle that circumscribes the tips of a multilobal filament to a radius (Ri) of a circle that is inscribed within the filament indentations. By the term "tip radius ratio" (TR) is meant the ratio of the radius (Rt) of the largest inscribed circle within a tip of a multilobal filament to that of the radius (Ri) of the largest inscribed circle within the filament. By the term "arm angle" (AA) is meant the acute angle ($\phi$) formed by the tangents to either side of a filament tip of a multilobal filament from a point on the line of symmetry for that tip. The significance of the symbols will be discussed later herein.

In general the individual filaments and yarn bundles of filaments to be characterized by the method of this invention may be prepared by extruding molten polymer or a solution of polymer through an orifice which provides a multilobal shape.

DETAILED DESCRIPTION OF THE ILLUSTRATED EMBODIMENTS

Figure 1:
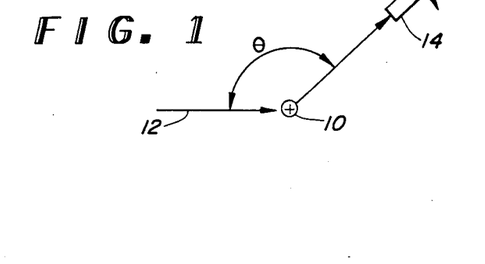
FIG. 1 is a schematic diagram of one mode for making scattered light analysis on multilobal filaments or yarns according to the invention.

Three measurement modes have been illustrated for making scattered light analysis on multilobal filaments or yarns according to the invention. In the first mode, as shown in FIG. 1, a sample filament or yarn 10 is mounted in a holder (not shown) that permits computer controlled-rotation of the sample 10 about its longitudinal axis with the sample positioned in the path of a normally incident beam of light 12. In this arrangement a detector 14 scans the sample 10 at one degree intervals of angle $\theta$ scanning from 6 to 176 degrees with respect to the direction of the incident beam 12 in a plane normal to the longitudinal axis of sample 10. At the conclusion of each detector scan, the sample is rotated 10 degrees about its axis. When the sample has been rotated through 360 degrees in these 10 degree increments the detected light intensities are averaged.

Figure 2:
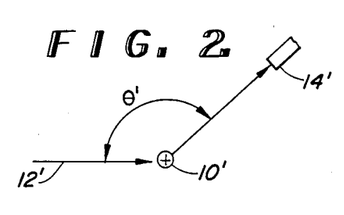
FIG. 2 is a schematic diagram of a second mode for making scattered light analysis on yarns containing multilobal filaments.

The second mode as shown in FIG. 2 differs from the first mode in that the detector 14' is fixed in a preselected position at an angle $\theta'$ and does not scan. A yarn 10' is moved in a path under tension through the focal point of the incident beam 12' which is in a plane perpendicular to the path of travel of the yarn. The light scattered from the yarn is detected by detector 14' in the same plane as the incident light.

Figure 3:
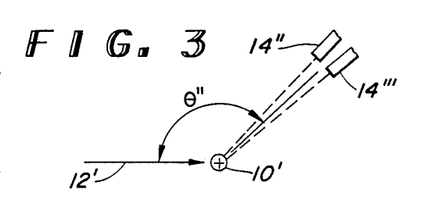
FIG. 3 is a schematic diagram of the preferred mode for making scattered light analysis on yarns containing multilobal filaments according to the invention.

The third mode as shown in FIG. 3 is essentially the same as the second mode of FIG. 2 except that two closely spaced detectors 14" and 14"' are positioned in a fixed relation from the point of incidence of the beam of light 12' at an angle $\theta''$ of about 128 degrees. The detectors 14", 14"' are preferably spaced about 6 degrees apart.

Figure 4:
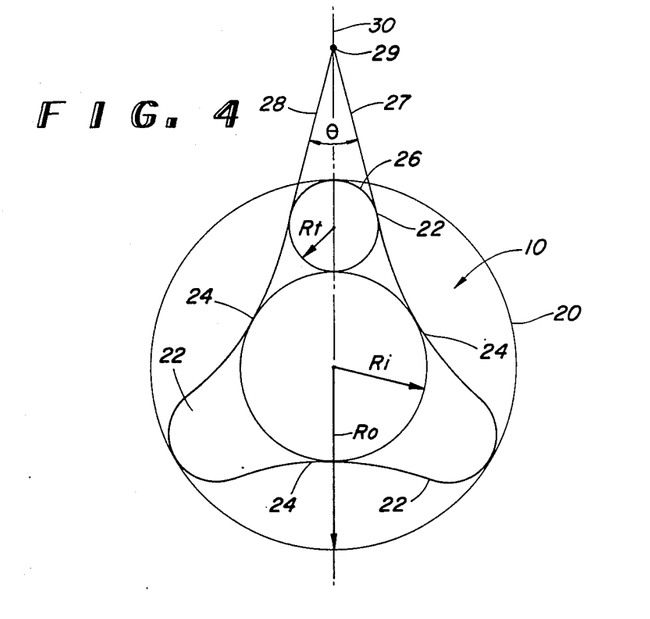
FIG. 4 is a schematic of an enlarged cross-sectional view of a trilobal filament having a shape characterized by the methods of the invention.

The terms modification ratio (MR), arm angle (AA) and tip radius ratio (TR) as defined above can be more fully understood by referring to FIG. 4 where (MR) relates to the ratio Ro/Ri wherein Ro is the radius of the circle 20 that circumscribes the tips 22 of the filament 10 and Ri is the radius of the circle that is inscribed within the indentations 24 of the filament 10. The tip radius ratio (TR) is the ratio of the radius Rt of the largest circle 26 contained within a tip 22 of filament 10 and arm angle (AA) is the acute angle $\phi$ formed by the tangents 27, 28 to either side of the filament tip 22 from a point 29 on the line of symmetry 30 for that tip.

OPTICAL ARRANGEMENT

Figure 5:
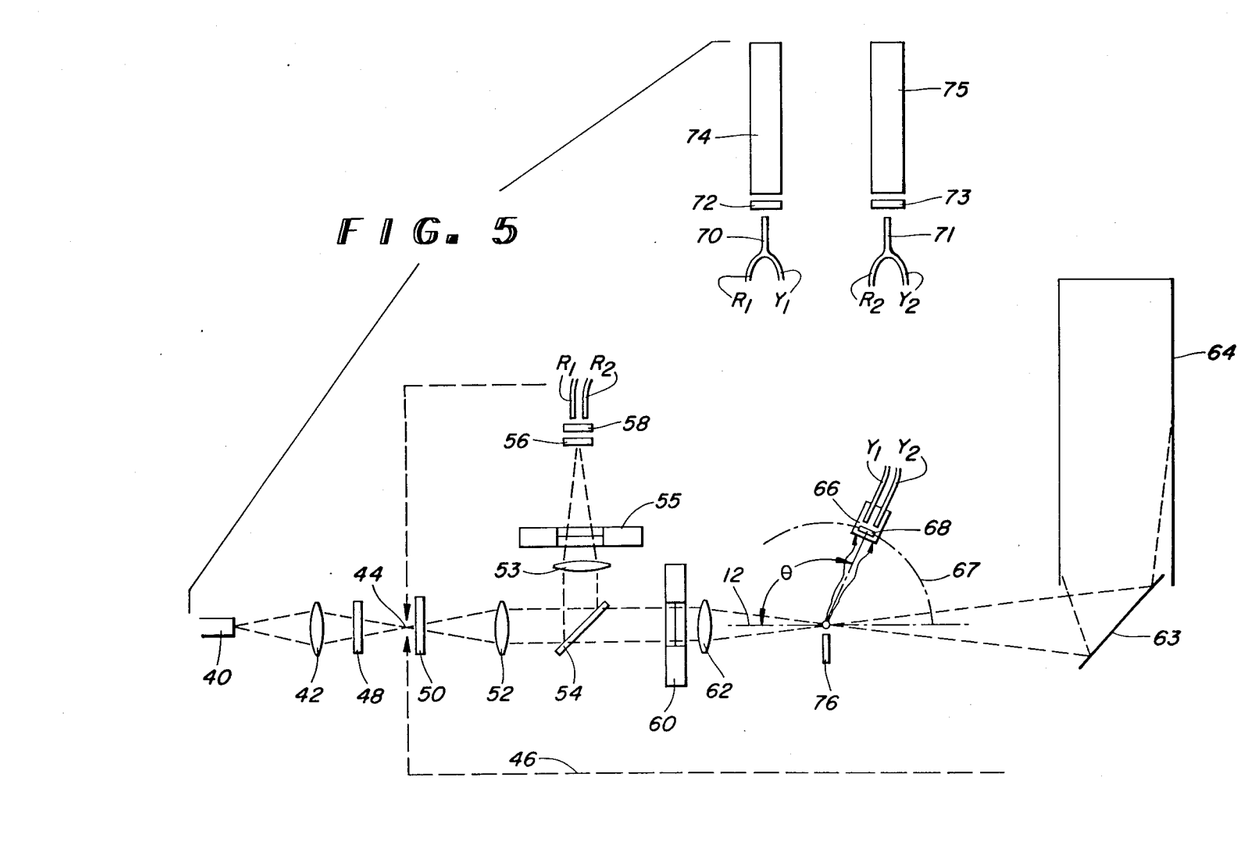
FIGS. 5, 6 and 7 are schematics of the optical system, the yarn transport system and the measurement control system of the preferred embodiment of this invention.
Figure 6:
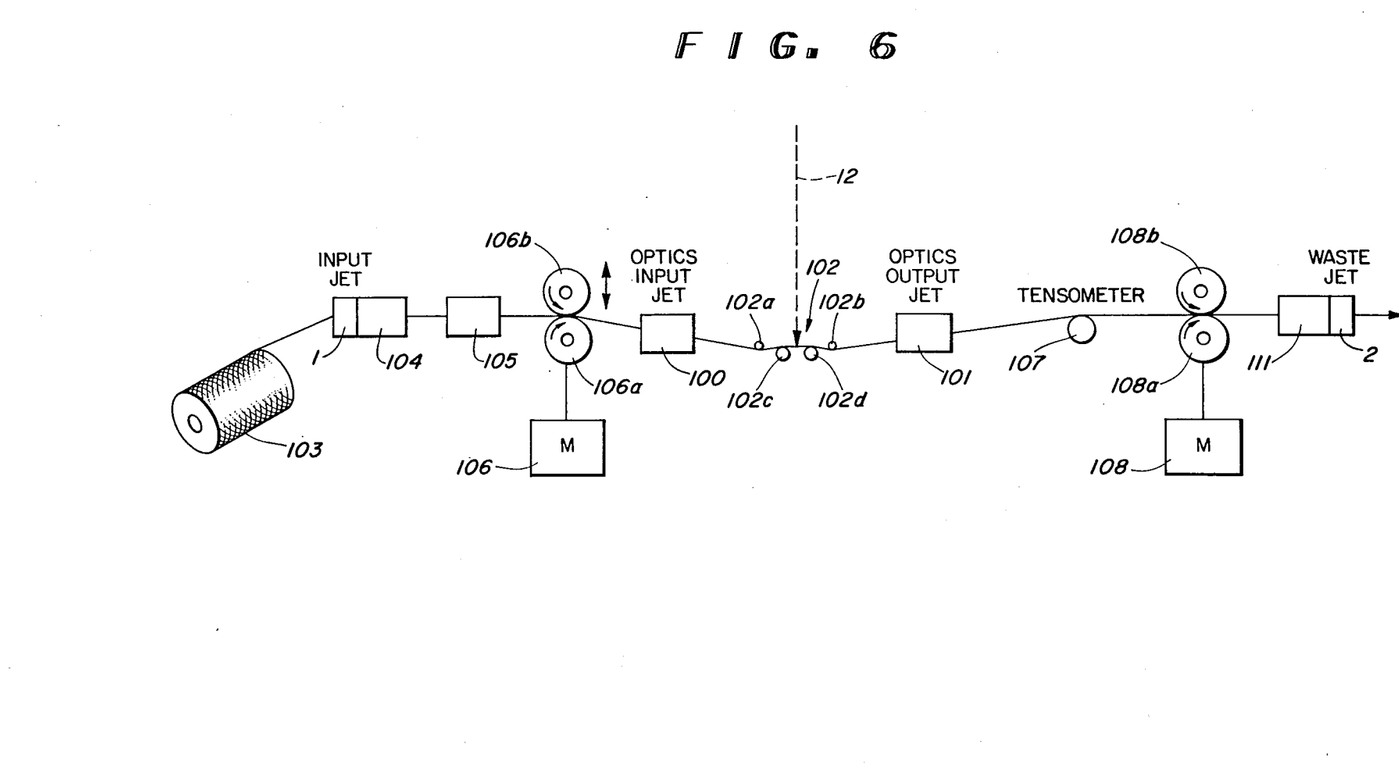
Figure 7:
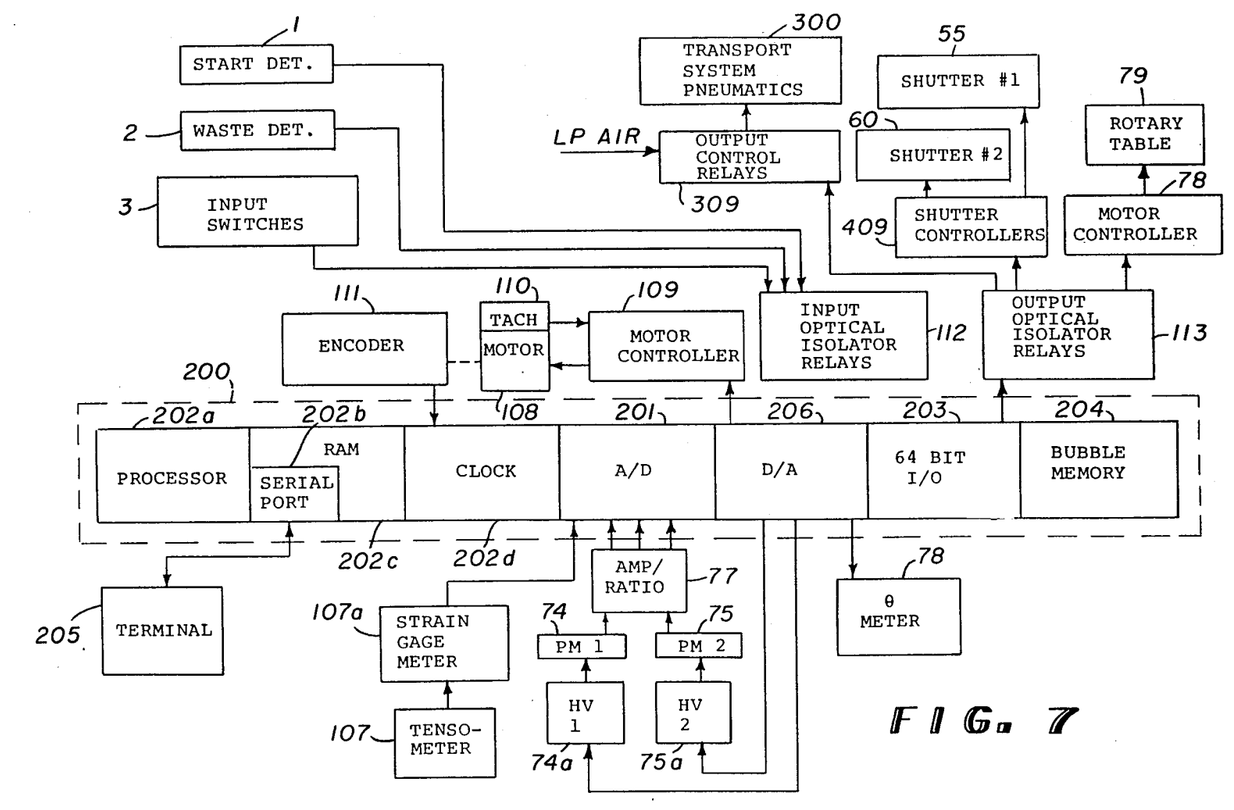

The apparatus chosen for purposes of illustration for analyzing the cross-sectional shape characteristics of a multilobal yarn includes an optical arrangement (FIG. 5), a transport system (FIG. 6) and a measurement control system (FIG. 7). Referring to FIG. 5, an optical arrangement is shown that can be operated to effect the preferred mode described in connection with FIG. 3. More particularly, light from a 100 watt quartz halogen lamp (i.e., white light source) 40 is focused by a lens 42 onto a slit 44 at the entrance of an optics housing, indicated generally as 46, via a low angle optical diffuser 48. A sharp cutoff filter 50 is located just downstream of slit 44 to eliminate ultra violet light from the light beam which might cause the yarn to fluoresce. Lens 52 collimates the light beam before it passes to beam splitter 54 which reflects a portion of the light beam, called the reference beam to a diffuser 56 via a focusing lens 53 and a computer activated shutter 55. The diffused light from diffuser 56 passes through a neutral density filter 58 into the receiving ends of two optical fibers $R_1$ and $R_2$.

The portion of the light beam transmitted by beam splitter 54, called the analytical beam, passes through a computer activated shutter 60 and lens 62 for focusing the light beam onto the moving yarn 12. Unscattered light passes to a light trap 64 for extinction via a reflector plate 63. Light scattered from the yarn 12 in the plane perpendicular to the path of travel of the yarn and in the plane of the incident beam is detected by detector housing 66 containing two closely spaced ends of optical fibers $Y_1$ and $Y_2$, each aligned with its own slit aperture and a hazy Mylar ® polyester film optical diffuser 68. The slit apertures allow reception of scattered light at two discrete angles, 5.7 degrees apart from one another.

Detector housing 66 is mounted for rotation in an arc 67 concentric with the longitudinal yarn axis. Preferably the housing is rotated through the range of about 40 degrees to 180 degrees as indicated by the angle $\theta$.

The optical fibers $R_1$ and $R_2$ with corresponding optical fibers $Y_1$ and $Y_2$ together comprise two sets of bifurcated fibers 70, 71. Each bifurcated fiber end addresses its respective photo multiplier 74, 75. Filters 72, 73 are used to match light levels at the optical fiber outputs to the characteristics of the individual photomultipliers.

Computer controlled shutters 55, 60 operate in a complementary fashion. With shutter 55 open and shutter 60 closed the analyzer can be calibrated for lamp drift and changes in sensitivity of both photomultipliers 74, 75 simultaneously. Diffuser 56 serves as a reference scatterer for this calibration, as it behaves as a uniform scatterer for both photomultipliers simultaneously. Similarly with shutter 60 open and shutter 55 closed, with standard calibrating diffuser 76 inserted into the analytical beam path at the yarn position with the detectors at some suitable angle such as 45°, the response of the photomultipliers 74, 75 can be measured. A measurement of stray light is made with both shutters 55 and 60 closed at the same time.

YARN TRANSPORT AND MEASUREMENT CONTROL SYSTEM

FIG. 6 is the general schematic for the yarn transport system of the reflectance analyzer. The purpose of the yarn transport system is to (1) convey the yarn sample at either a selected constant tension or a constant differential nip roll speed through the beam path and (2) to enable automatic stringup of the yarn with the apparatus without the need for human intervention.

At the input end of the yarn transport system, yarn from package 103 is sensed by a yarn sensor 1 incorporated into jet 104 as the yarn end is fed into the inlet end of the jet. This occurrence turns on air to jets 100, 101, 111, and 104. The latter jet propels the yarn end through pneumatic-controlled cutter 105, then through the opened first set of rotating transport rolls 106a, 106b; through optics input and output jets 100 and 101, and after passing through a second set of rotating transport rolls 108a, 108b, through jet 111 to a waste receptacle. After a yarn sensor 2 incorporated in jet 111 senses the passing yarn, air to input jet 104 is turned off and the motion of the propelled yarn is picked up by driven transport roll 106b, when it is lowered by pneumatic means against nip roll 106a. Both rolls 106a and 106b are driven by a constant speed synchronous motor 106. In the span between the jet 100 and jet 101, two movable optics pins 102a and 102b are lowered to increase the wrap angle over the two fixed guide pins 102c, 102d for making the running yarn taut in the measurement zone 102.

Constant tension control of the running yarn is based on measurements made at the exit of jet 101 by means of a tensiometer 107, typically a cantilever pin type disclosed in U.S. Pat. No. 4,295,360. The tensiometer 107 is pneumatically moved against the running yarn to sense yarn tension as the optics pins 102a, 102b are lowered and the transport rolls 108a and 108b close. Referring to FIG. 7 the analog voltage signals produced by tensiometer 107 and strain gauge meter 107a are input to an analog to digital (A/D) convertor 201 for conversion into the format required by computer 202a. Proportional control of yarn tension is effected by changing the instantaneous rotational speed of rolls 108a, 108b, via servomotor 108, which is electrically controlled by controller 109, typically Aerotech 4020B with tachometer 110 attached to provide shaft rotation feedback. A shaft encoder 111, connected to motor 108, inputs pulses to clock module 202d for use by D/A module 206 which generates an analog feedback signal to controller 109 to maintain constant roll speed. The result is that servomotor 108 rotates rolls 108a, 108b at a constant speed to provide a constant draw ratio for the running yarn. In the other mode constant yarn tension is maintained using the signal from tensiometer 107 and strain gauge meter 107a via A/D module 201 and D/A module 206, as feedback to controller 109.

Yarn detectors 1 and 2 are positioned to sense the feeding of a yarn end at the inlet of jet 101 and the appearance of the yarn end at the waste jet 111 outlet, respectively. The yarn detector signals pass via a set of optical isolaters 112, and a DEC, 64 bit I/O module 203 (typically a DEC DRV-11-J) before they are input to computer 202a.

As indicated by block 300 in FIG. 7, the pneumatically operated components of the transport system of FIG. 6 including jets 104, 100, 101, and 111; pneumatically operated cutter 105; and pneumatically raised and lowered transport rolls 106b, and 108b; optics guide pins 102a, 102b, and tensiometer pin 107 are all totally controlled by a bank of 24 volt solid state relay operated valves that are contained in pneumatic controller 309. Low pressure air is furnished to the valves from a common air manifold while the valve operating signals, received from the I/O module 203 via output optical isolators 113, control the solid state relays for operating the valve solenoids in proper sequence.

In addition to output control relays 309, the I/O module, furnishes analytical and reference beam shutter control signals via optical isolators 113 to the shutter controller circuitry 409 for operating shutters 55 and 60 as well as positioning information to the stepping motor controller 78 for positioning rotary table 79. The azimuth of the detector arm which carries detector housing 66 in its arcuate path is read out on an angle display meter 78.

Computer system 200 comprises a DEC PDP-11/23 computer 202a; an A/D converter 201; an I/O digital interface module 203; a random access memory 202c; a bubble memory 204; a serial data input port 202b that is tied-in with a terminal 205; a D/A converter 206; and a real time clock 202d. All units communicate with computer 202a via a DEC Q-Bus. Data input functions are principally derived via A/D converter 201 and the clock 202d. The photomultiplier tubes 74 and 75, which are typically type 9824A's manufactured by EMI-Gencom Corp., send their outputs to the amplifier and ratio circuitry 77. An Analog Devices 436B analog divider contained in circuit 77 ratios the separate output signals of photomultipliers 74 and 75. The ratio $I_1/I_2$ as well as the independent outputs of photomultipliers 74 and 75 appear on input lines 00, 01 and 02 to A/D converter 201 for entry into the computer at signalled times. During the photomultiplier tube calibration phase, when the shutter 60 to analytical beam is closed and the reference beam optics shutter 55 is open, the computer 202a compares the two measured photomultiplier tube values with their corresponding set points. Upon signal from digital to analog converter 206 the results are applied to modify the high voltage operating points of the individual photomultiplier tubes by adjusting the outputs of power supplies 74a and 75a.

Figure 8:
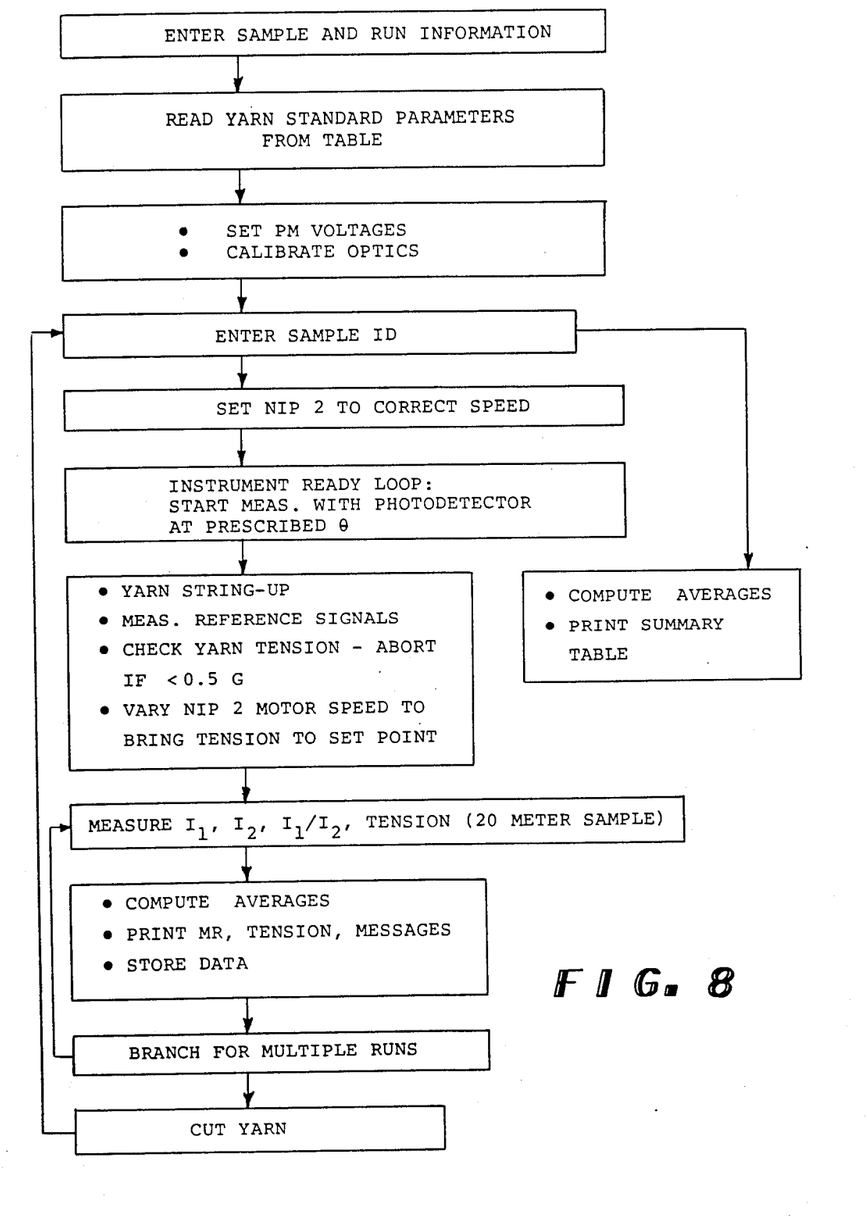
FIG. 8 is a block diagram of the operating mode of this invention.

The keyboard terminal 205 enables the operator to conveniently enter yarn type information while the bubble memory 204 provides software and parameter storage as well as temporary data storage. Referring to FIG. 8, at the outset of each run, the operator enters on keyboard 205 sample and run information for the yarns to be analyzed in terms of yarn type codes. Associated with each yarn type code is a unique set of tabulated yarn standard parameters stored in bubble memory 204 that includes: linear correlation coefficients for relating scattering intensity values to a particular cross-sectional feature; a nominal value of MR; a tension set point value; and the prescribed azimuth $\theta$ for detector housing 66.

Next, the computer initiates a calibration procedure. With shutter 55 open, and shutter 60 closed, the reference signals obtained via optical fibers $R_1$ and $R_2$ and respective photomultipliers 74 and 75 are measured and the respective PMT high voltage power supplies 74a and 75a are automatically adjusted by the computer to bias the outputs to preset constant voltage levels. After the power supply adjustments, the computer causes detector housing 66 to move into position $\theta = 45°$, and closes both shutters 55 and 60 to record stray light signal levels, $VS_i$ (i=1,2,3). These are obtained by measuring the low level light intensities at the output of optical fibers $Y_1$ and $Y_2$ as determined by the respective outputs of PMT 74 (i=1), PMT 75 (i=2) and their ratio (i=3).

Similarly, the reference signal levels $VR_i$ (i=1,2,3) are recorded with shutter 55 open and shutter 60 closed. Then with shutter 55 again closed and shutter 60 open, the computer signals standard diffuser plate 76 to move into the analytic beam path to obtain reading $VD_i$ (i=1,2,3). To conclude the calibration phase, the computer computes a series of calibration factors from the equation:

$$F_i = C\left(\frac{VR_i - VS_i}{VD_i - VS_i}\right) \quad (i = 1,2,3) \tag{1}$$

where C is a predetermined geometric optics constant.

After completing the instrument calibration, the operator enters into computer 202a the identification of the yarn sample to be analyzed. This step automatically recalls values from the previously stored yarn standard parameter set. From this set, a nominal speed for motor #2, 108 (via motor #2 controller 109) is prescribed, which meets the prescribed yarn tension setpoint. (After string up, constant yarn tension is maintained in the face of periodic tension fluctuations by controlling the speed of motor #2, 108, to respond instantaneously to the changes sensed by tensiometer 107.) Further, in response to another value in the standard yarn parameter set, the computer automatically positions detector assembly 66 to a unique azimuth $\theta$ (via motor controller 78 and rotary table 79) to obtain the best correlation of scattering ratio $I_1/I_2$ to MR for that yarn.

The operator next introduces the sample yarn end from package 103 to the inlet of input jet 104 to initiate the yarn string up sequence. In addition to jet 104, jets 100, 101, and 111 are simultaneously activated as soon as the start detector 1 senses the operator's hand. Input jet 104 propels the yarn end through the cutter 105, the nip of constant speed rolls 106, through jet 100 at the inlet side of the optics compartment 46, across the guide pins 102 in the optics zone, through jet 101 at the outlet side of the optics compartment 46, through the nip of variable speed transport rolls 108 and into a waste receptacle (not shown) at the outlet of jet 111. Upon sensing the yarn end's arrival in jet 111, the second yarn detector 2 produces a signal to computer 202a to shut off the air supply to jet 104; to lower nip roll 106b; to raise tensiometer 107 against the running yarn; to lower nip roll 108b; to lower optics pins 102a, 102b; and to turn off jets 100, 101, in seriatim.

During the yarn string up, the reference signal levels $VR_i$ (i=1,2,3) are again measured. Furthermore, if during string up yarn tension should be less than 0.5 grams, as measured by tensiometer 107, then the run is aborted. The cause of low tension could indicate, for example, that a yarn wrap or break condition exists. Variable speed motor #2, 108, varies its rotation rate in response to commands from motor #2 controller, 109, to bring to constant tension the particular yarn type to be measured.

The measurement phase commences when constant yarn tension has been attained and terminates when the instantaneous yarn scattering intensity values $VY_i$ (i=1,2,3) have been recorded over the length of the run, typically 20 meters. The operator may direct the computer to branch to repeat the measurements to obtain confirmation of the preceding data set(s). When measurements are complete, a software sequence activates cutter 105 and the yarn in the instrument is exhausted to waste, via waste jet 111.

Once the values $VY_i$ (i=1,2,3) have been recorded, separate normalized averages of $I_1$, $I_2$ and $I_1/I_2$ and their standard deviations about the means are computed and displayed with the calculated MR values. The normalized values of $I_1$ and $I_2$ and $I_1/I_2$ are given by:

$$X_i = F_i \left( \frac{VY_i - VS_i}{VR_i - VS_i} \right) \quad (2)$$

where $X_i$ is one of $I_1$, $I_2$ or $I_1/I_2$.

Further, an average MR over the sampled yarn length is obtained by inverting the equation $I_1/I_2 = A \cdot MR + B$, where linear correlation coefficients A and B have been determined in advance from empirical data for a particular yarn type with a known cross-sectional characteristic. Thus, $$\overline{MR} = \frac{\left[ \frac{1}{N} \sum_{i=1}^{N} \frac{I_1}{I_2} \right] - B}{A} \quad (3)$$

where N is the number of samples obtained during the run, and $\overline{MR}$ is average modification ratio, taken over N samples.

EXAMPLE

Six 40-13 T-865 SD flat trilobal nylon filament yarns with different cross-sectional shape characteristics were prepared. The filament cross-sectional shape of these yarns was examined by one or more known methods and by the third mode of the present invention.

A thin slice of each yarn was cut perpendicular to its longitudinal axis with a microtome and mounted on a microscope slide by techniques well known in the art. Two photomicrographs of each yarn cross-section were made at a magnification such that together the two photomicrographs clearly showed each of the 13 filaments making up the yarn bundle. The perimeter of the image of the individual filaments on the photomicrographs was traced using a commercial digitizer (such as Numonics Model 224). The digitizer translates the perimeter tracing into x-y data pairs from which MR and TR are calculated using a small computer. The mean MR and TR determined from the digitizer tracing of the 13 filaments comprising each yarn are tabulated below in Table I.

TABLE I

| Sample No. | MR | TR |
|---|---|---|
| Y1 40-21 | 1.66 | .32 |
| Y2 33-14 | 1.62 | .33 |
| Y3 29-21 | 1.49 | .37 |
| Y4 29-11 | 1.49 | .39 |
| Y5 01-14 | 1.40* | .41* |
| Y6 01-11 | 1.46 | .40 |

*Digitizer tracings were made for (only) 11 of the 13 filaments for sample Y5.

A 20 yard length of each of the above six yarns was characterized with an apparatus having the optical arrangement depicted in FIG. 5 and the transport system depicted in FIG. 6 and using the third mode of the present invention as shown in FIG. 3.

Figure 9:
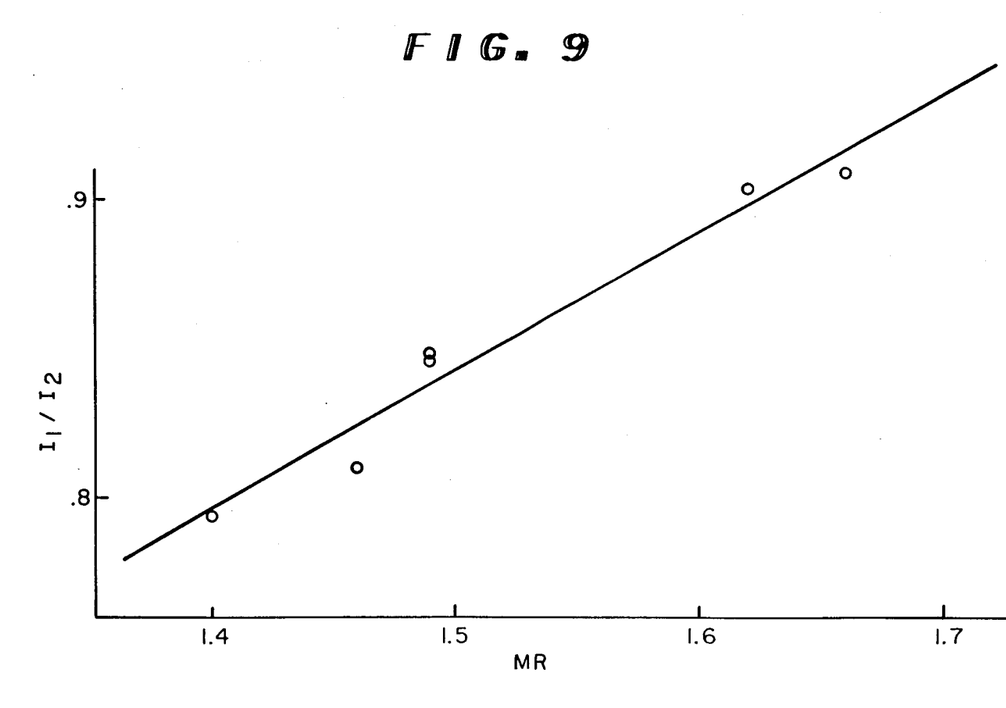
FIG. 9 is a graph showing correlation between modification ratio of trilobal filaments and scattered light intensity as per the Example.

Accordingly, for the six yarns Y1, Y2 ... Y6, the two fixed detectors were spaced 5.7° apart at an average scattering angle $\theta$ of about 128°. On the 20 yard long yarn sample running at 1 yd/sec, repeated measurements of intensity, $I_1$ and $I_2$, were made at fixed angles $\theta_1 = 125.1°$ and $\theta_2 = 130.8°$, respectively. The values of $I_1/I_2$ are recorded in Table II for the six yarns. In FIG. 9 is plotted $I_1/I_2$ versus the MR values determined by the digitizer. A straight line, of the form $I_1/I_2 = a \cdot MR + b$, with a high correlation coefficient, is obtained over this rather wide range of MR values. MR values of other 40-13 T865 SD yarns are then determined by measuring $I_1/I_2$ as just described and using the calibration curve (FIG. 9) of the linear relationship.

TABLE II

| Sample No. | $I_1/I_2$ |
|---|---|
| Y1 40-21 | 0.908 |
| Y2 33-14 | 0.903 |
| Y3 29-21 | 0.848 |
| Y4 29-11 | 0.846 |
| Y5 01-14 | 0.794 |
| Y6 01-11 | 0.810 |

I claim:

1. A method for measuring average cross sectional shape parameters such as modification ratio for a yarn bundle of multilobal filaments comprising:
   moving the yarn in a path under tension;
   directing an incident beam of light onto the yarn in a plane perpendicular to said path;
   detecting the light scattered from the yarn in said plane at a position at an angle from the incident beam of light;
   measuring the intensity of the scattered light detected at said position; and
   determining the average modification ratio of said yarn from a calibration curve based on said intensity.

2. The method of claim 1 wherein said position is located between about 6 degrees and 176 degrees from said incident beam.

3. The method of claim 1 wherein said incident beam is white light.

4. Method for measuring average cross sectional shape parameters such as modification ratio for a yarn of multilobal filaments comprising:
   moving the yarn in a path under tension;
   directing an incident beam of light onto said yarn in a plane perpendicular to said path;
   detecting the light scattered from the yarn in the plane of the incident light at first and second spaced angular positions relative to a prescribed angle from the incident beam;
   measuring the intensity of the scattered light at said first and second positions; and
   determining the average modification ratio of said yarn from a calibration curve based on ratioing the intensity of scattered light measured at said first position and the intensity of scattered light measured at said second position.

5. The method of claim 4 wherein said first and second positions are spaced apart by about six degrees about said angle from the incident beam.

6. The method of claim 1 or 4 wherein said angle from the incident beam is about 128 degrees.

7. A method for measuring average cross sectional shape parameters such as modification ratio for a monofilament comprising:
   moving the monofilament in a path under tension;

directing an incident beam of light onto the monofilament in a plane perpendicular to said path;
detecting the light scattered from the monofilament in said plane at a position at an angle from the incident beam of light;

measuring the intensity of the scattered light detected at said position; and
determining the average modification ratio of said monofilament from a calibration curve based on said intensity.

* * * * *